United States Patent
Ichihara et al.

(10) Patent No.: US 9,212,188 B2
(45) Date of Patent: Dec. 15, 2015

(54) METHOD FOR PRODUCING ALICYCLIC DIEPOXY COMPOUND

(71) Applicants: JX Nippon Oil & Energy Corporation, Tokyo (JP); OSAKA UNIVERSITY, Suita-shi, Osaka (JP)

(72) Inventors: Junko Ichihara, Suita (JP); Shunro Yamaguchi, Suita (JP); Atsushi Kameyama, Tokyo (JP); Takashi Suzuki, Tokyo (JP); Takashi Morikita, Tokyo (JP)

(73) Assignees: JX Nippon Oil & Enery Corporation, Tokyo (JP); OSAKA UNIVERSITY, Suita-shi, Osaka (JP)

( * ) Notice: Subject to any disclaimer, the term of this patent is extended or adjusted under 35 U.S.C. 154(b) by 0 days.

(21) Appl. No.: 14/402,376

(22) PCT Filed: Apr. 26, 2013

(86) PCT No.: PCT/JP2013/062355
§ 371 (c)(1),
(2) Date: Nov. 20, 2014

(87) PCT Pub. No.: WO2013/175936
PCT Pub. Date: Nov. 28, 2013

(65) Prior Publication Data
US 2015/0141675 A1    May 21, 2015

(30) Foreign Application Priority Data
May 22, 2012  (JP) .................................. 2012-116389

(51) Int. Cl.
| C07D 301/03 | (2006.01) |
| C07D 493/04 | (2006.01) |
| C07D 301/12 | (2006.01) |
| B01J 23/30  | (2006.01) |

(52) U.S. Cl.
CPC ............... *C07D 493/04* (2013.01); *B01J 23/30* (2013.01); *C07D 301/12* (2013.01)

(58) Field of Classification Search
CPC ..... C07D 493/04; C07D 301/12; B01J 23/30; B01J 31/34
USPC ....................................................... 549/544
See application file for complete search history.

(56) References Cited

U.S. PATENT DOCUMENTS 5,430,161 A * 7/1995 Brown et al. ................. 549/531
2010/0113807 A1  5/2010 Ichihara et al.

FOREIGN PATENT DOCUMENTS

| JP | S62-234550 A | 10/1987 |
| JP | 2003-238545 A | 8/2003 |
| JP | 2004-182648 A | 7/2004 |
| JP | 2010-235649 A | 10/2010 |
| WO | 2008093711 A1 | 8/2008 |

OTHER PUBLICATIONS

Okovytyy et al. "Identification of the stereoisomers of tetrahydroindene diepoxide by the 1H and 13C NMR characteristics: A combined experimental and theoretical study," Journal of Molecular Structure: THEOCHEM, vol. 730, No. 1-3, pp. 125-132 (2005).
Matoba et al. "Epoxidation of cyclic diolefins with hydrogen peroxide catalyzed by areneseleninic acid," Journal of Japan Petroleum Institute, vol. 26, No. 5, pp. 349-354 (1983).
Int'l Search Report issued Jun. 11, 2013 in Int'l Application No. PCT/JP2013/062355.

* cited by examiner

*Primary Examiner* — T. Victor Oh
(74) *Attorney, Agent, or Firm* — Panitch Schwarze Belisario & Nadel LLP

(57) ABSTRACT

The present invention provides a method for producing an alicyclic diepoxy compound at a higher yield by carrying out epoxidation of an alicyclic olefin compound at a higher reaction rate. The method is a method for producing an alicyclic diepoxy compound represented by formula (1) below by reacting an alicyclic olefin compound represented by formula (2) below with hydrogen peroxide in the coexistence of the alicyclic olefin compound represented by formula (2) below, a hydrogen peroxide solution, a powdered solid catalyst support and a powdered solid catalyst all together:

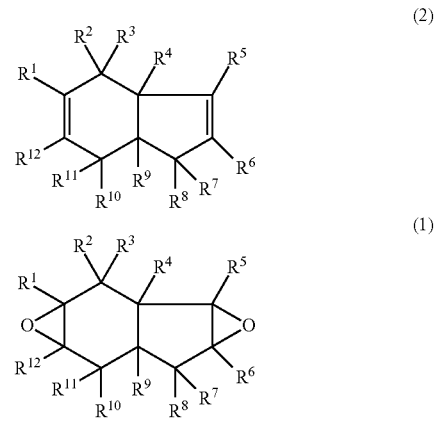

wherein $R^1$ to $R^{12}$ are each hydrogen, halogen, an alkyl group optionally having halogen or an alkoxy group optionally having a substituent.

6 Claims, No Drawings

METHOD FOR PRODUCING ALICYCLIC DIEPOXY COMPOUND

CROSS-REFERENCE TO RELATED APPLICATION

This application is a Section 371 of International Application No. PCT/JP2013/062355, filed Apr. 26, 2013, which was published in the Japanese language on Nov. 28, 2013, under International Publication No. WO 2013/175936 A1, and the disclosure of which is incorporated herein by reference.

TECHNICAL FIELD

The present invention relates to a method for producing an epoxy compound from an olefin compound and hydrogen peroxide. More specifically, the present invention relates to a method for producing an alicyclic diepoxy compound from an alicyclic olefin compound in the presence of a solid catalyst support and a solid catalyst.

BACKGROUND ART

Currently, various types of diepoxy compounds having an alicyclic skeleton per molecule are commercially available. Such diepoxy compounds are reacted with various curing agents and curing catalysts to produce cured products. These cured products of the diepoxy compounds can possess characteristics such as heat resistance, transparency and excellent dielectric characteristics peculiar to resins produced from compounds having an alicyclic skeleton, and these epoxy compounds are useful as components of coating agents, adhesives, inks or sealants or intermediates for producing compounds which are useful in the various final applications such as pharmaceutical agents or medical products.

Whilst, tetrahydroindene has been known to be by-produced upon synthesis of vinylnorbornene through a reaction of cyclopentadiene and 1,3-butadiene. In recent years, effective uses of tetrahydroindene have been sought.

For example, Patent Literature 1 discloses a method for producing a diepoxide of tetrahydroindene that is an epoxy compound having two alicyclic skeletons per molecule, from tetrahydroindene. Epoxy compounds with an alicyclic skeleton having no ester group in the molecule have been, therefore, demanded.

As a method for producing an epoxy compound, a method is known, in which olefins are oxidized with peracids such as peracetic acid. However, this method has problems that peracids require careful handling, and epoxides are reacted with carboxylic acids present in the reaction system thereby producing esters and the like, resulting in a decrease in the selectivity of the epoxides, and also that in production of an alicyclic epoxy compound regarded as having a high reactivity with acids, coexisting organic acids are likely reacted with epoxy groups produced in the presence of water, resulting in a decrease in the selectivity of the epoxides due to the ring-opening of the epoxy groups, and that the post-treatments are troublesome. Therefore, a method has been attracting attention, which uses hydrogen peroxide as an oxidation agent, which is easy in handling and turns to water that is harmless after the reaction.

As a method for producing an epoxy compound from olefins using hydrogen peroxide, a method is known in which epoxidation is carried out by reacting olefins and a hydrogen peroxide solution with a halogenated hydrocarbon as a solvent using a catalyst such as polyacids (Patent Literature 1). This method, however, has problems concerning halogen impurities in the products and environmental load due to the use of the halogenated hydrocarbon.

Patent Literature 3 discloses a solid phase reaction system for oxidation comprising a mixture of a powdered solid catalyst support and a powdered solid catalyst for oxidation reaction, an organic compound and a hydrogen peroxide solution.

CITATION LIST

Patent Literature

Patent Literature 1: Japanese Patent Application Laid-Open Publication 2004-182648

Patent Literature 2: Japanese Patent Application Laid-Open Publication No. 62-234550

Patent Literature 3: WO2008/093711

SUMMARY OF INVENTION

Technical Problem

The present invention has an object to provide a method for producing an alicyclic diepoxy compound at a higher yield by carrying out epoxidation of an alicyclic olefin compound at a higher reaction rate.

Solution to Problem

The present invention relates to a method for producing an alicyclic diepoxy compound represented by formula (1) below by reacting an alicyclic olefin compound represented by formula (2) below with hydrogen peroxide in the coexistence of the alicyclic olefin compound represented by formula (2) below, a hydrogen peroxide solution, a powdered solid catalyst support and a powdered solid catalyst all together:

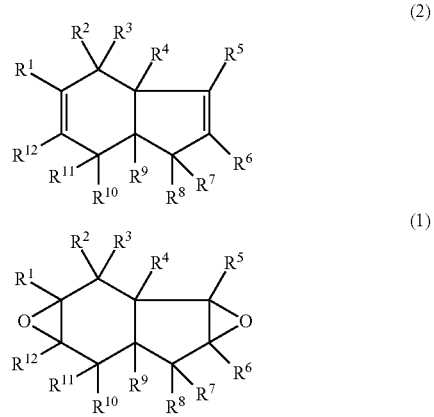

wherein $R^1$ to $R^{12}$ are each hydrogen, halogen, an alkyl group optionally having halogen or an alkoxy group optionally having a substituent.

The present invention also relates to the foregoing method for producing an alicyclic diepoxy compound wherein the alicyclic olefin compound is a compound represented by formula (4) below and the alicyclic diepoxy compound is a compound represented by formula (3) below:

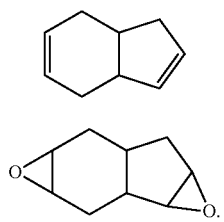

(4)

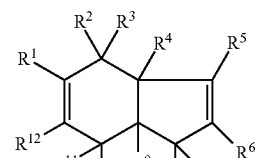

(3)

The present invention also relates to the foregoing method for producing an alicyclic diepoxy compound wherein the solid catalyst is selected from the group consisting of: oxides of metals selected from the group consisting of tungsten, molybdenum and vanadium; oxoacids containing metals selected from the group consisting of tungsten, molybdenum and vanadium and salts thereof; and oxides, halides and sulfates of elements selected from the group consisting of iron, manganese and ruthenium.

The present invention also relates to the foregoing method for producing an alicyclic diepoxy compound wherein the solid catalyst is selected from the group consisting of oxides of tungsten or molybdenum, isopolyacids containing tungsten or molybdenum and heteropolyacids containing tungsten or molybdenum and particularly relates to the foregoing method for producing an alicyclic diepoxy compound wherein the solid catalyst is an isopolyacid containing tungsten.

The present invention also relates to the foregoing method for producing an alicyclic diepoxy compound wherein the solid catalyst support is selected from the group consisting of phosphates, diatomaceous earth, silica, alumina, kaolin, silica-alumina and calcium fluoride and particularly relates to the foregoing method for producing an alicyclic diepoxy compound wherein the solid catalyst support is apatite.

Advantageous Effect of Invention

The method of the present invention can produce an industrially valuable alicyclic diepoxy compound represented by formula (1) at a higher reaction rate and yield and has advantages that it can reduce environmental loads caused by wastewater or organic solvents and can reuse the catalyst. The method of the present invention also has features that the solid catalyst and solid catalyst support constituting the solid phase can be reused by simply drying them after removal of the product so that no step making the reaction operation complicated is required upon reuse of the catalyst and isolation or recovery of the product is easily carried out.

DESCRIPTION OF EMBODIMENTS

Preferable embodiments of the present invention will be described below.

The present invention is a method for producing an alicyclic diepoxy compound represented by formula (1) below by reacting an alicyclic olefin compound represented by formula (2) below with hydrogen peroxide in the coexistence of the alicyclic olefin compound represented by formula (2) below, a hydrogen peroxide solution, a powdered solid catalyst support and a powdered solid catalyst all together:

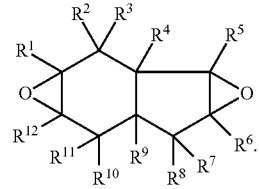

(2)

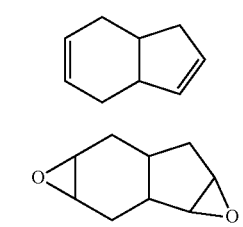

(1)

In formulas (1) and (2), $R^1$, $R^2$, $R^3$, $R^4$, $R^5$, $R^6$, $R^7$, $R^8$, $R^9$, $R^{10}$, $R^{11}$ and $R^{12}$ are each independently hydrogen, halogen, an alkyl group which may have a substituent or an alkoxy group which may have a substituent.

The alkyl group is preferably an alkyl group having 1 to 10 carbon atoms, more preferably an alkyl group having 1 to 4 carbon atoms. When the alkyl group has a substituent, examples thereof include halogens and alkoxy groups.

The alkoxy group is preferably an alkoxy group having 1 to 10 carbon atoms, more preferably an alkoxy group having 1 to 4 carbon atoms. When the alkoxy group has a substituent, examples thereof include halogens and alkoxy groups.

$R^1$ to $R^{12}$ are each independently preferably, hydrogen, fluorine, an alkyl group or an alkoxy group, more preferably hydrogen or fluorine, more preferably hydrogen.

That is, the alicyclic olefin compound is preferably a compound represented by formula (4) below from which an alicyclic diepoxy compound represented by formula (3) below is produced.

(4)

(3)

The present invention uses a mixture of a powdered solid catalyst support and a powdered solid catalyst to which a hydrogen peroxide solution and a compound represented by formula (2) are added so as to contact with each other so that the compound of formula (2) is oxidized thereby producing an alicyclic diepoxy compound represented by formula (1). The method of the present invention does not use peracid unlike methods as disclosed in Patent Literature 1 and thus can simplify post-treatment and decrease environmental loads. Furthermore, since no carboxylic acid is contained in the system, the method can suppress the production of esters and alcohols and is higher in epoxidation selectivity. Furthermore, the method of the present invention is higher in selectivity of a diepoxy compounds in an oxidation reaction and needs no complicated treatment process, making it possible to recover the diepoxy compound without production loss.

The solid catalyst support may be powders of solid materials having properties that they disperse a solid catalyst, a hydrogen peroxide solution and a compound represented by formula (2), are not degraded thereby and do not disturb the oxidation reaction, preferably those having properties to facilitate the oxidation reaction. Specific examples include phosphates such as apatite, clays such as diatomaceous earth [main component: silica], kaolin [main component: silica-alumina] and hydrotalcite, fluorides such as calcium fluoride, and oxides of silica, titania or alumina. Among these, a solid catalyst support selected from phosphates, diatomaceous earth, silica, alumina, kaolin, silica-alumina and calcium fluoride is preferably used because they can achieve a higher yield. In particular, a solid catalyst support selected from apatite, diatomaceous earth and calcium fluoride can achieve a particularly higher yield.

Herein, the apatite is a kind of calcium phosphate, and fluorapatite, chiorapatite, carbonate apatite and hydroxyapatite exist as apatite-type minerals. Among these, hydroxyapatite and fluorapatite are preferably used.

The diatomaceous earth is a soft rock or soil composed mainly of a husk of Bacillariophyta, and contains silica as a main component but also often alumina, ferric oxide, alkali metal oxides in addition to silica. Alternatively, those which are porous and have a high porosity and a cake bulk density of about 0.2 to 0.45 are often used. Among diatomaceous earths, calcined products or freshwater diatomaceous earths are preferred but other diatomaceous earths may be used. Specific examples of such diatomaceous earths include those marketed under the tradename of Celite (registered trademark) by Celite Corporation and marketed under the tradename of Celatom by Eagle Pitcher Minerals, Inc. Alternatively, those calcined together with sodium carbonate may also be used.

Examples of the solid catalyst include: oxides of metals selected from the group consisting of tungsten, molybdenum and vanadium; oxoacids containing metals selected from the group consisting of tungsten, molybdenum and vanadium and salts thereof; and oxides, halide and sulfates of elements selected from the group consisting of iron, manganese and ruthenium.

Examples of the oxides of metals selected from the group consisting of tungsten, molybdenum and vanadium include $WO_3$, $MoO_3$ and $V_2O_5$. Examples of the oxoacids containing metals selected from the group consisting of tungsten, molybdenum and vanadium and salts thereof include tungstic acid ($H_2WO_4$) and tungstates such as $Na_2WO_4$, molybdenum acid ($H_2MoO_4$) and molybdates such as $Na_2MoO_4$, vanadic acid and vanadates such as $NH_4VO_3$, isopolyacids containing tungsten, molybdenum or vanadium and salts thereof, and heteropolyacids containing tungsten, molybdenum or vanadium and salts thereof. Isopolyacids or heteropolyacids containing tungsten, molybdenum or vanadium also include mixtures represented by $Q_3[PW6Mo_6O_{40}]$ and $Q_7[PV_4Mo_8O_{40}]$ and peroxo-type compounds represented by $Q_3\{PO_4[W(O)(O_2)]_4\}$ and $Q_2[W_2O_3(O_2)_4]$ (in these formulae, Q represents a counter cation).

Examples of the hetero atom of the heteropolyacids include phosphorus, boron, silicone, germanium, lanthanoid elements, manganese, nickel, iron, cobalt or ruthenium. Examples of the counter cations of the isopolyacid salts or heteropolyacid salts include organic cations such as tetrabutylammonium, butylammonium, benzyltrimethylammonium, cetyltrimethylammonium and cetylpyridinium and inorganic cations such as ammonium, potassium, sodium and calcium.

More specifically, examples of the isopolytungstic acids containing tungsten include $(NH_4)_6W_7O_{24}$, $(NH_4)_{10}[H_2W_{12}O_{42}]$, $(CetylNMe_3)_7(NH_4)_3[H_2W_{12}O_{42}]$, $(CetylNMe_3)_{10}[H_2W_{12}O_{42}]$, $(CetylPy)_9(NH_4)[H_2W_{12}O_{42}]$, $(CetylPy)_{10}[H_2W_{12}O_{42}]$, $(CetylPy)_4[W_{10}O_{32}]$ and $K_4[W_{10}O_{32}]$, and examples of the heteropolytungstic acids containing tungsten include $(CetylPy)_3[PW_{12}O_{40}]$, $(CetylPy)_5H_2[PW_{11}O_{39}]$ and $Na_9[PW_9O_{34}]$ and also those produced by replacing phosphorus (P) in the above-described heteropolytungstic acids with boron (B), silicon (Si) or germanium (Ge). $CetylNMe_3$ and CetylPy in the formulae represent cetyltrimethylammonium and cetylpyridinium, respectively.

Examples of the oxoacid containing molybdenum and salts thereof include compounds produced by replacing tungsten in the compounds exemplified above as oxoacid containing tungsten and salts thereof, with molybdenum. Examples of the oxoacid containing vanadium and salts thereof include compounds produced by replacing tungsten in the compounds exemplified above as the oxoacid containing tungsten and salts thereof, with vanadium.

Among these solid catalysts, preferred are catalysts selected from the group consisting of oxides of tungsten or molybdenum, isopolyacids containing tungsten or molybdenum and heteropolyacids containing tungsten or molybdenum and particularly preferred are catalysts selected from the group consisting of isopolyacids and heteropolyacids containing tungsten because a higher selectivity can be achieved with these catalysts.

Examples of the oxides, halides or sulfates of elements selected from the group consisting of iron, manganese and ruthenium include $FeCl_3$, $MnSO_4$ and $RuCl_3$.

The solid catalyst is not required to be immobilized to the solid catalyst support, and all what needs to be done is that the powdered solid catalyst is simply mixed with the powdered solid catalyst support. For example, the powdered solid catalyst is added in advance to the powdered solid catalyst support and then stirred and mixed thereby producing a mixture of the solid catalyst and solid catalyst support. No particular limitation is imposed on the particle sizes of the powdered solid catalyst and powdered solid catalyst support. Those having a particle size of about 5 to 100 μm, which are easily available may be used thereby achieving the advantageous effects of the present invention such as a higher yield of the product.

The amount of the solid catalyst is preferably 5 to 60 percent by mass, more preferably 10 to 50 percent by mass of the solid catalyst support. With 5 percent by mass or less of the catalyst, the compound represented by formula (1) cannot be produced at a high yield because the reaction rate is decreased. With more than 60 percent by mass of the catalyst, the yield cannot be improved, and thus it is industrially disadvantageous.

Next, a compound represented by formula (2) to be oxidized and a hydrogen peroxide solution are added to the mixture of the powdered solid catalyst support and the powdered solid catalyst produced as described above. This addition is so carried out that both of them are dispersed in the above-described mixture and come into mutual contact. For example, they may be mixed, stirring so that they are dispersed and come into mutual contact well. Thereafter, they may be reacted, allowing to stand or alternatively mixed and stirred.

The hydrogen peroxide solution may be used in an amount of about 1 to 10 mmol as hydrogen peroxide of 1 mmol of the double bond site of the compound represented by formula (2), but the amount is desirously from 1.2 to 5 mmol. Less than 1 mmol of the hydrogen peroxide solution results in lack of hydrogen peroxide while more than 10 mmol of the hydrogen peroxide solution results in a decrease in the yield of an epoxy compound due to ring-opening of the epoxides.

The solid catalyst support and solid catalyst may be used in an amount of about 0.01 to 5 g on the basis of 1 mmol of the compound represented by formula (2) but desirously used in an amount of 0.05 to 3.0 g.

In the present invention, the hydrogen peroxide solution is used at a concentration of preferably 5 to 60 percent by mass, more preferably 5 to 35 percent by mass. In the case of using a hydrogen peroxide solution of a low concentration in a method for producing an epoxy compound using hydrogen peroxide, the produced epoxide is hydrolyzed to produce by-products such as diols and the like, resulting in the reduced selectivity of the intended product. However, the method of the present invention is high in selectivity and can produce the intended product at a higher yield even in the case of using a hydrogen peroxide solution of low concentration.

Handling of a hydrogen peroxide solution at a concentration of 35 to 60 percent by mass involves danger to an extent that transportation thereof is regulated, and a two phase heterogeneous reaction system requires some reaction equipment that can sufficiently avoid the occurrence of rapid exothermic reaction or explosion. However, the method of the present invention enables the reaction to be carried out more safely with a practical yield of the product by impregnating the solid phase with a hydrogen peroxide solution.

An organic solvent may be further added to the mixture of the powdered solid catalyst support and powdered solid catalyst before, after or simultaneously with adding thereto the compound represented by formula (2) and the hydrogen peroxide solution. The use of the organic solvent can restrain epoxides and water from contacting mutually so as to be likely to avoid the produced epoxides from ring-opening. The organic solvent is added in an amount of 0 to 200 percent by mass on the basis of the compound represented by formula (2). More than 200 percent by mass of the organic solvent causes the reaction rate to reduce and thus causes the yield of a diepoxy compound represented by formula (1) to decrease.

Examples of the organic solvent include aliphatic hydrocarbons, aromatic hydrocarbons, alcohols, ethers, esters, ketones, nitrile, amides and the like. The organic solvent is preferably ethanol, ethyl acetate, hexane or toluene, particularly preferably toluene.

In the present invention, the oxidation reaction temperature is preferably from 0 to 50° C., more preferably 5 to 40° C. At lower than 0° C., the reaction proceeds slowly while at higher than 50° C., it causes the yield to decrease due to deactivation of the solid catalyst or ring-opening of the epoxides.

The reaction time is generally preferably from 1 to 24 hours, more preferably 1 to 12 hours. With a reaction time of shorter than 1 hour, the reaction does not proceed sufficiently and thus decreases the yield while with a reaction time of longer than 24 hours, the productivity decreases.

In the present invention, the conversion rate of the compound represented by formula (2) is preferably 80% or greater, and the yield of the compound represented by formula (1) is preferably 50% or greater.

No particular limitation is imposed on the method for isolating the produced diepoxy compound represented by formula (1). For example, a method may be used wherein the epoxy compound is solvent-extracted and then concentrated.

The chlorine content of the diepoxy compound represented by formula (1) produced by the present invention is preferably 100 ppm by mass or less, more preferably 10 ppm by mass or less because the compound when formed into a cured resin product can be further improved in moisture proof reliability. The chlorine content is the value measured in accordance with JIS, K-7243-3, specifically the value measured by dissolving a sample (an epoxy compound) in diethylene glycol monobutyl ether and saponifying the solution with a potassium hydroxide alcohol solution, heating it to reflux, followed by potentiometric titration with a silver nitrate solution.

The chlorine content of the epoxy compound can be reduced by purification by distillation, or alternatively by a method such as alkali aqueous solution washing or absorbent treatment.

The metal content of the diepoxy compound represented by formula (1) produced by the present invention is preferably 100 ppm by mass or less, more preferably 10 ppm by mass or less because a cured resin product produced from the compound is further enhanced in mechanical characteristics and electrical characteristics. The metal content can be measured by analyzing a 10% toluene solution of a sample (an epoxy compound) with inductively-coupled plasma emission (ICP emission). The apparatus for the measurement may be Optima 4300DV manufactured by Perkin-Elmer Corp. In this measurement, quantitative analysis of each metal species detected by qualitative analysis can be carried out using a commercially available metal standard solution.

The metal content of the epoxy compound can be reduced by purification by distillation, or alternatively by a method such as alkali aqueous solution washing or absorbent treatment.

EXAMPLES

The present invention will be described in more detail with the following examples but is not limited thereto.

Example 1

Into a screw-top test tube were weighed out 1.0 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 25° C. After the mixture was allowed to stand at 25° C. for 2 hours, the resulting reaction mixture was extracted with hexane (5 mL×3 times) and the solvent was distilled out from the extracted solution thereby producing 0.14 g of tetrahydroindene diepoxide, which was a colorless transparent solution. The yield was 93%.

Example 2

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 25° C. After the mixture was allowed to stand at 25° C. for 2 hours, the resulting reaction mixture was extracted with hexane (5 mL×3 times) and the solvent was distilled out from the extracted solution thereby producing 0.14 g of tetrahydroindene diepoxide, which was a colorless transparent solution. The yield was 89%.

Example 3

Into a screw-top test tube were weighed out 2.0 g of apatite that is a solid catalyst support and 0.056 g (0.010 mmol) of (CetylPy)$_9$(NH$_4$)[H$_2$W$_{12}$O$_{42}$] that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 25° C. After the mixture was allowed to stand at 25° C. for 6 hours, the resulting reaction mixture was extracted with hexane (5 mL×3 times) and the solvent was distilled out from the extracted solution thereby producing 0.12 g of tetrahydroindene diepoxide, which was a colorless transparent solution. The yield was 81%.

Example 4

Into a screw-top test tube were weighed out 0.50 g of apatite that is a solid catalyst support and 0.085 g (0.015 mmol) of (CetylPy)$_9$(NH$_4$)[H$_2$W$_{12}$O$_{42}$] that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 15° C. After the mixture was allowed to stand at 15° C. for 3 hours, the resulting reaction mixture was extracted with hexane (5 mL×3 times) and the solvent was distilled out from the extracted solution thereby producing 0.15 g of tetrahydroindene diepoxide, which was a colorless transparent solution. The yield was 98%.

Example 5

Into a screw-top test tube were weighed out 2.0 g of apatite that is a solid catalyst support and 0.074 g (0.015 mmol) of (CetylPy)$_{10}$[H$_2$W$_{12}$O$_{42}$] that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 15° C. After the mixture was allowed to stand at 15° C. for 3 hours, the resulting reaction mixture was extracted with hexane (5 mL×3 times) and the solvent was distilled out from the extracted solution thereby producing 0.15 g of tetrahydroindene diepoxide, which was a colorless transparent solution. The yield was 94%.

Example 6

Into a screw-top test tube were weighed out 0.50 g of apatite that is a solid catalyst support and 0.074 g (0.015 mmol) of (CetylNMe$_3$)$_7$(NH$_4$)$_3$[H$_2$W$_{12}$O$_{42}$] that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 15° C. After the mixture was allowed to stand at 15° C. for 3 hours, the resulting reaction mixture was extracted with hexane (5 mL×3 times) and the solvent was distilled out from the extracted solution thereby producing 0.14 g of tetrahydroindene diepoxide, which was a colorless transparent solution. The yield was 95%.

Comparative Example 1

To 0.17 g (0.05 mmol) of H$_3$PW$_{12}$O$_{40}$.nH$_2$O that is a solid catalyst were added 5.74 g (50 mmol) of a 30% hydrogen peroxide solution, and the catalyst was dissolved by stirring at 60° C. for 30 minutes.
Into an eggplant flask equipped with a condenser tube were added and dissolved 2.8 g (23 mmol) of tetrahydroindene, 0.051 g (0.15 mmol) of cetylpyridinium chloride monohydrate and 20 ml of chloroform. The total amount of the hydrogen peroxide solution of the solid catalyst was added to the mixture and stirred at 25° C. for 40 minutes. The oil phase was separated and the water phase was extracted with 2×2 ml of chloroform. The extract and oil phase were mixed and washed with 2×8 ml of a 10% sodium thiosulfate aqueous solution, 2×8 ml of a 5% sodium carbonate aqueous solution and 2×8 ml of water. The solvent was distilled out from the washed mixture of the extract and oil phase thereby producing 0.24 g of tetrahydroindene diepoxide, which was a colorless transparent solution. The yield was 7%.

INDUSTRIAL APPLICABILITY

The present invention can produce an alicyclic diepoxy compound represented by formula (1) that is industrially highly valuable at a higher reaction rate and yield.

The invention claimed is:

1. A method for producing an alicyclic diepoxy compound represented by formula (1) below by reacting an alicyclic olefin compound represented by formula (2) below with hydrogen peroxide in the coexistence of the alicyclic olefin compound represented by formula (2) below, a hydrogen peroxide solution, a powdered solid catalyst support and a powdered solid catalyst all together:

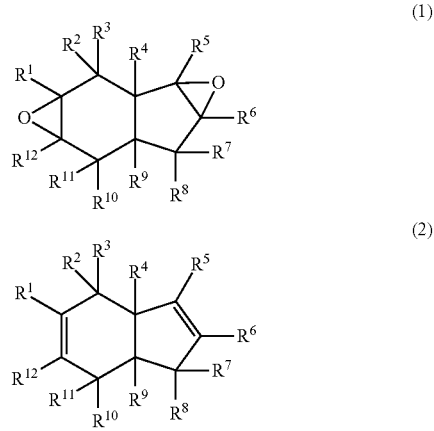

wherein R1 and R12 are each hydrogen, halogen, an alkyl group optionally having halogen or an alkoxy group optionally having halogen or an alkoxy group as a substituent, and wherein the powdered solid catalyst is selected from the group consisting of isopolytungstic acids containing cetyltrimethylammonium as a cation and isopolytungstic acids containing (NH$_4$)[H$_2$W$_{12}$O$_{42}$] and an organic cation selected from the group consisting of tetrabutylammonium, butylammonium, benzyltrimethylammonium, and cetylpyridinium.

2. The method for producing an alicyclic diepoxy compound according to claim 1, wherein the alicyclic olefin compound is a compound represented by formula (4) below and the alicyclic diepoxy compound is a compound represented by formula (3) below:

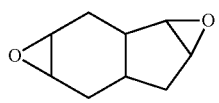

(3)

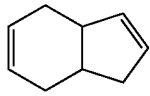

(4)

3. The method for producing an alicyclic diepoxy compound according to claim 1 wherein the solid catalyst support is selected from the group consisting of phosphates, diatomaceous earth, silica, alumina, kaolin, silica-alumina and calcium fluoride.

4. The method for producing an alicyclic diepoxy compound according to claim 1 wherein the solid catalyst support is apatite.

5. The method for producing an alicyclic diepoxy compound according to claim 1 wherein the powdered solid catalyst is $(CetylNMe_3)_7(NH_4)_3[H_2W_{12}O_{42}]$ or $(CetylNMe_3)_{10}[H_2W_{12}O_{42}]$.

6. The method for producing an alicyclic diepoxy compound according to claim 1 wherein the powdered solid catalyst is $(CetylPy)_9(NH_4)[H_2W_{12}O_{42}]$.

* * * * *